US010292799B2

(12) United States Patent
Sergi

(10) Patent No.: US 10,292,799 B2
(45) Date of Patent: May 21, 2019

(54) TOOTH WHITENING DEVICE

(71) Applicant: Chiara Domenica Sergi, Savignano sul Rubicone (IT)

(72) Inventor: Chiara Domenica Sergi, Savignano sul Rubicone (IT)

( * ) Notice: Subject to any disclaimer, the term of this patent is extended or adjusted under 35 U.S.C. 154(b) by 43 days.

(21) Appl. No.: 15/028,870

(22) PCT Filed: Oct. 14, 2014

(86) PCT No.: PCT/IB2014/002373
§ 371 (c)(1),
(2) Date: Apr. 12, 2016

(87) PCT Pub. No.: WO2015/056090
PCT Pub. Date: Apr. 23, 2015

(65) Prior Publication Data
US 2016/0250011 A1  Sep. 1, 2016

(30) Foreign Application Priority Data

Oct. 16, 2013  (IT) ................................ FI2013A0245
Oct. 16, 2013  (IT) ................................ FI2013A0246

(51) Int. Cl.
*A61C 19/06*  (2006.01)
*A61C 3/025*  (2006.01)
(Continued)

(52) U.S. Cl.
CPC ............ *A61C 19/066* (2013.01); *A61C 3/025* (2013.01); *A61C 17/022* (2013.01);
(Continued)

(58) Field of Classification Search
CPC ... A61C 16/066; A61C 3/025; A61C 17/0202; A61C 17/227; A61M 11/02;
(Continued)

(56) References Cited

U.S. PATENT DOCUMENTS

2002/0004190 A1* 1/2002 Diasti .................. A61C 19/066
433/215
2002/0123020 A1* 9/2002 Aumuller ............... A61C 3/025
433/88

(Continued)

FOREIGN PATENT DOCUMENTS

| JP | H07 328035 A | 12/1995 |
|---|---|---|
| JP | H07328035 A | 12/1995 |
| WO | 2013/093798 A1 | 6/2013 |
| WO | 2013/093816 A1 | 6/2013 |

*Primary Examiner* — Heidi M Eide
(74) *Attorney, Agent, or Firm* — Pearne & Gordon LLP

(57) ABSTRACT

This invention relates to a device for whitening teeth, including both a tank (16) for at least part of the whitening product in solid or semi-solid form, and a tank (17) of a product in liquid form and means designed to mix the products in powder form and in liquid form before they come out of a nozzle (14), the device also includes a duct (18) leading to the nozzle (14) and operatively connected to a pressurized energy source (219) from which, on command, a flow of gas extends; operatively connected in an intermediate position of a first stretch (18A) of the duct (18) there being the tank (16) of at least part of the whitening product; operatively connected in an intermediate position of a second stretch (18B) of the duct (18) there being the tank (17) of product in liquid form.

4 Claims, 3 Drawing Sheets

(51) Int. Cl.
*A61C 17/22* (2006.01)
*A61C 17/02* (2006.01)
*A61C 17/022* (2006.01)
*A61M 11/02* (2006.01)
*A61M 11/06* (2006.01)

(52) U.S. Cl.
CPC ........ *A61C 17/0202* (2013.01); *A61C 17/227* (2013.01); *A61M 11/02* (2013.01); *A61M 11/06* (2013.01); *A61M 2202/0468* (2013.01); *A61M 2202/064* (2013.01); *A61M 2210/0637* (2013.01)

(58) Field of Classification Search
CPC .......... A61M 11/06; A61M 2202/0468; A61M 2202/064; A61M 2210/0637
See application file for complete search history.

(56) References Cited

U.S. PATENT DOCUMENTS

| | | | |
|---|---|---|---|
| 2008/0280260 A1 | 11/2008 | Belikov et al. | |
| 2009/0246730 A1 | 10/2009 | Takamori et al. | |
| 2010/0248179 A1 | 9/2010 | Sogaro | |
| 2010/0254915 A1* | 10/2010 | Kao | A61K 8/19 424/49 |
| 2010/0261135 A1* | 10/2010 | Feine | A61C 17/20 433/86 |
| 2014/0308625 A1 | 10/2014 | Fairley et al. | |

* cited by examiner

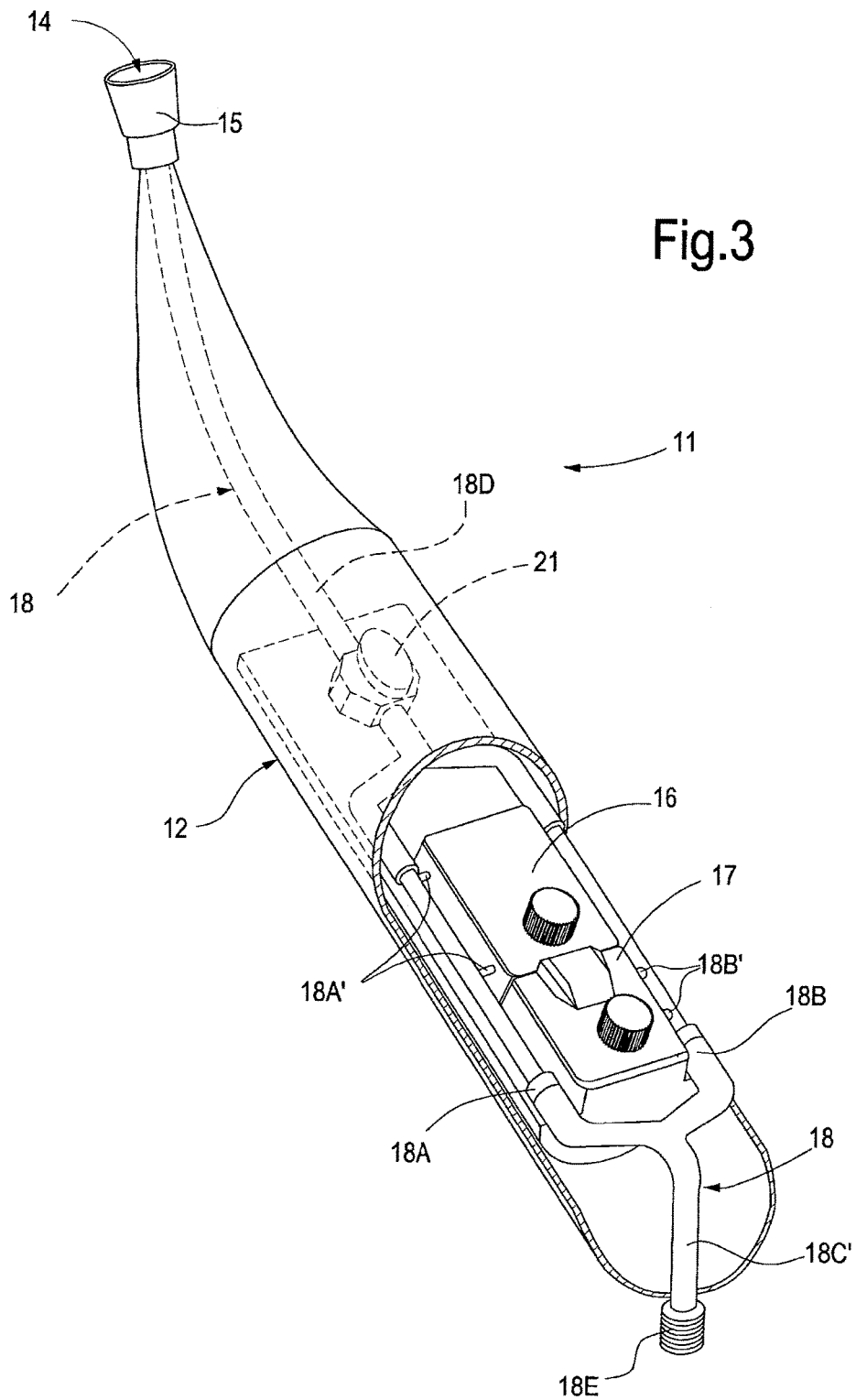

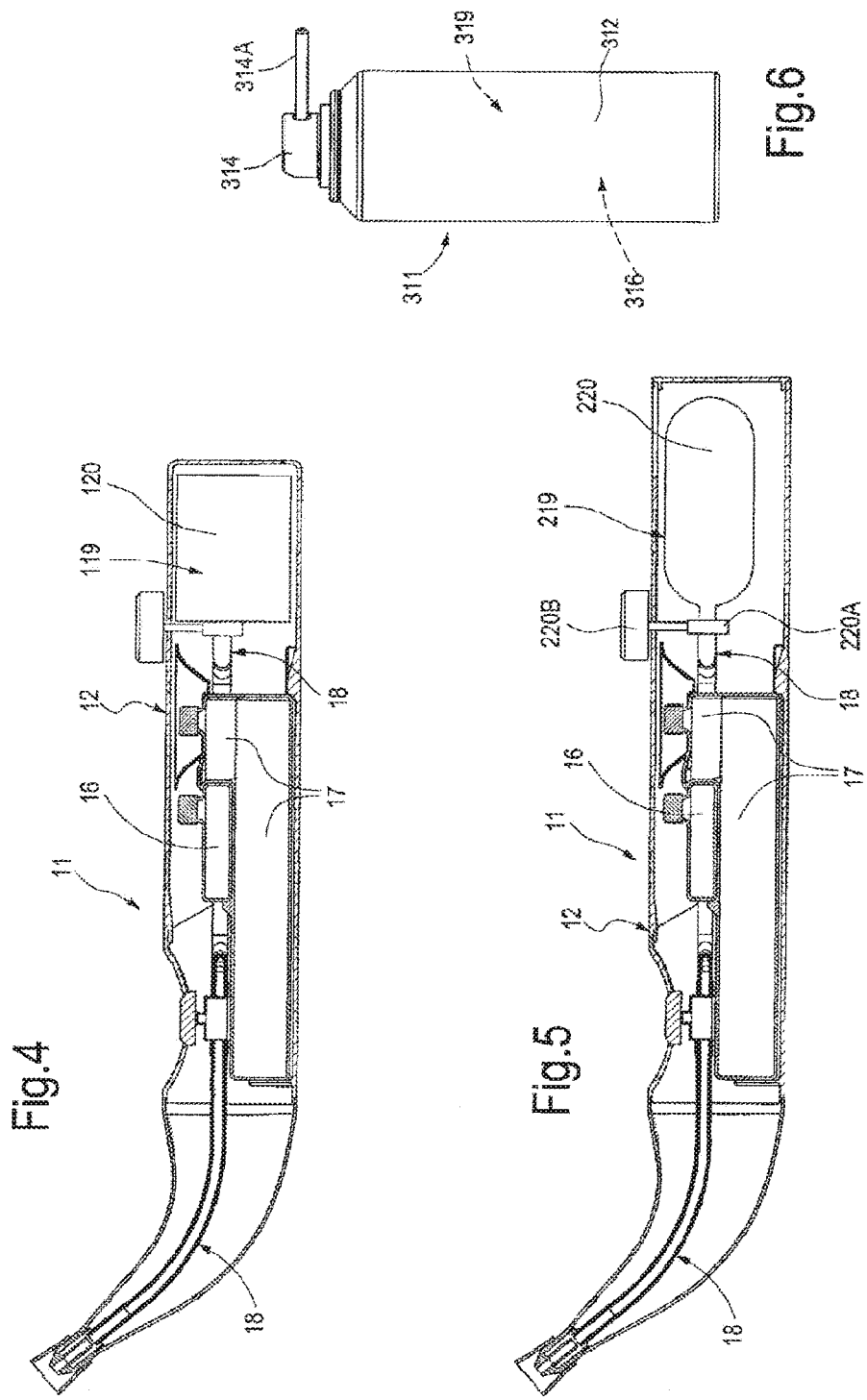

TOOTH WHITENING DEVICE

TECHNICAL FIELD

This invention relates to systems for whitening teeth. More particularly, the invention relates to a device for whitening teeth which comprises a dispenser equipped with a zone to be gripped by the user and a nozzle for ejecting a flow of whitening product emitted thanks to a pressure source, which can be used in a home environment.

BACKGROUND

In recent years there has been an increase in the need to have increasingly whiter teeth.

There are now many professional techniques used by dentists to whiten teeth: hydrogen peroxide-based whitening gels, ultraviolet ray laser lamps, whitening strips and even ceramic veneers applied to the vestibular surface of the tooth, treated to resist yellowing.

There are also prior art devices for whitening teeth for use in a surgery environment, having a console, inside which there is a compressor and a tank of whitening powder, a handpiece which the operator can use on the patient whose teeth need whitening, and a flexible hose connecting the handpiece to the console. The operator activates the device and from the handpiece, through a suitable nozzle, a flow of whitening powder comes out towards the teeth of the patient. The powder comes from the tank and is conveyed by the flow of air produced by the compressor through the flexible hose.

This type of device is particularly bulky and cannot be used in a home environment, since it is not very practical and must be controlled by specialised personnel.

DISCLOSURE OF THE INVENTION

The aim of this invention is to provide a whitening device which is particularly compact.

Another important aim of this invention is to provide a whitening device which is easy to use.

Yet another aim of this invention is to provide a whitening device which can be used in a home environment.

A further aim of this invention is to provide a whitening device which can be used without dangers for the user.

Another aim of this invention is to provide a whitening device which can be used frequently by a user without particular contraindications.

Therefore this invention relates to a device for whitening teeth, comprising a dispenser equipped with a zone to be gripped by the user and a nozzle for ejecting a flow of whitening product, characterised in that it comprises a tank of at least part of the whitening product, fixed to said dispenser in such a way as to move together with said dispenser during the movements of the hand of the user, and a pressure energy source of the type which can be used until finished, designed to allow the whitening product to come out. Said device comprising both a tank for at least part of the whitening product in solid or semi-solid form, and a tank of a product in liquid form and means designed to mix said products in powder form and in liquid form before they come out of the nozzle. Said device comprises a duct leading to said nozzle and operatively connected to said pressurised energy source from which, on command, a flow of gas extends. Operatively connected in an intermediate position of a first stretch of said duct is the tank of at least part of the whitening product, therefore the passage of the flow of gas through that intermediate position of said first stretch of duct causes the suction and intake into the duct of said at least part of the whitening product by Venturi effect. Operatively connected in an intermediate position of a second stretch of said duct is said tank of product in liquid form. Therefore the passage of the flow of gas through said intermediate position of said second stretch of duct causes the suction and intake into the duct of said product in liquid form by Venturi effect. Said at least part of the whitening product and said product in liquid form mix before coming out of the nozzle.

Preferably, according to the invention, said dispenser may be a spray can containing whitening product and a pressurised gas. Preferably, said ejecting nozzle is provided on the valve of said spray can.

Advantageously according to the invention said whitening product may be in the form of powder or a liquid mixture comprising: sodium acid carbonate, preferably between 70% and 90% of the weight of the compound, pink Himalayan salt, preferably between 5% and 30% of the weight of the compound, in the case of a liquid mixture, water or physiological salt solution, preferably between 5% and 20% of the weight of the compound; one or more of the following essential oils preferably being present: lemon essential oil between 0.2 and 2% of the weight of the compound, sage essential oil between 0.2 and 1% of the weight of the compound, peppermint essential oil between 0.2 and 2% of the weight of the compound.

Furthermore, according to the invention, said whitening product may comprise abrasive diamond powder.

The invention also relates to use of a spray can for whitening teeth, by application of whitening product using an ejecting nozzle directly on the teeth, said can containing a whitening product mixture.

This invention also relates to a device for whitening teeth, comprising a dispenser equipped with a zone to be gripped by the user and a nozzle for ejecting a flow of whitening product, characterised in that it comprises a tank of at least part of the whitening product, fixed to said dispenser in such a way as to move together with said dispenser during the movements of the hand of the user, and a pressure energy source comprising a compressor; said device comprising both a tank for at least part of the whitening product in solid or semi-solid form, and a tank of a product in liquid form and means designed to mix said products in powder form and in liquid form before they come out of the nozzle. Said device comprises a duct leading to said nozzle and operatively connected to said pressurised energy source from which, on command, a flow of gas extends. Operatively connected in an intermediate position of a first stretch of said duct is the tank of at least part of the whitening product, therefore the passage of the flow of gas through that intermediate position of said first stretch of duct causes the suction and intake into the duct of said at least part of the whitening product by Venturi effect. Operatively connected in an intermediate position of a second stretch of said duct is said tank of product in liquid form. Therefore the passage of the flow of gas through said intermediate position of said second stretch of duct causes the suction and intake into the duct of said product in liquid form by Venturi effect. Said at least part of the whitening product and said product in liquid form mix before coming out of the nozzle.

Preferably according to the invention said whitening product may be in the form of powder or a liquid mixture comprising: sodium acid carbonate, preferably between 70% and 90% of the weight of the compound, pink Himalayan salt, preferably between 5% and 30% of the weight of the compound, in the case of a liquid mixture, water or physiological salt solution, preferably between 5% and 20% of the weight of the compound; one or more of the following essential oils preferably being present: lemon essential oil between 0.2 and 2% of the weight of the compound, sage essential oil between 0.2 and 1% of the weight of the compound, peppermint essential oil between 0.2 and 2% of the weight of the compound.

Furthermore, according to the invention, said whitening product may comprise abrasive diamond powder.

BRIEF DESCRIPTION OF THE DRAWINGS

Further details and advantages of the invention are more apparent from the description which follows of a preferred, non-limiting embodiment, illustrated by way of example, but without limiting the scope of the invention, in the accompanying drawings, in which:

FIG. 3 is an axonometric, cutaway view of the dispenser of the preceding figures;

FIG. 4 is a longitudinal section of a whitening product dispenser of another embodiment, alternative to that of FIG. 1;

FIG. 5 is a longitudinal section of a whitening product dispenser of an embodiment of the device according to the invention;

FIG. 6 is a longitudinal section of a whitening product dispenser in the form of a spray can, according to the invention.

DETAILED DESCRIPTION OF PREFERRED EMBODIMENTS OF THE INVENTION

Figure 1:
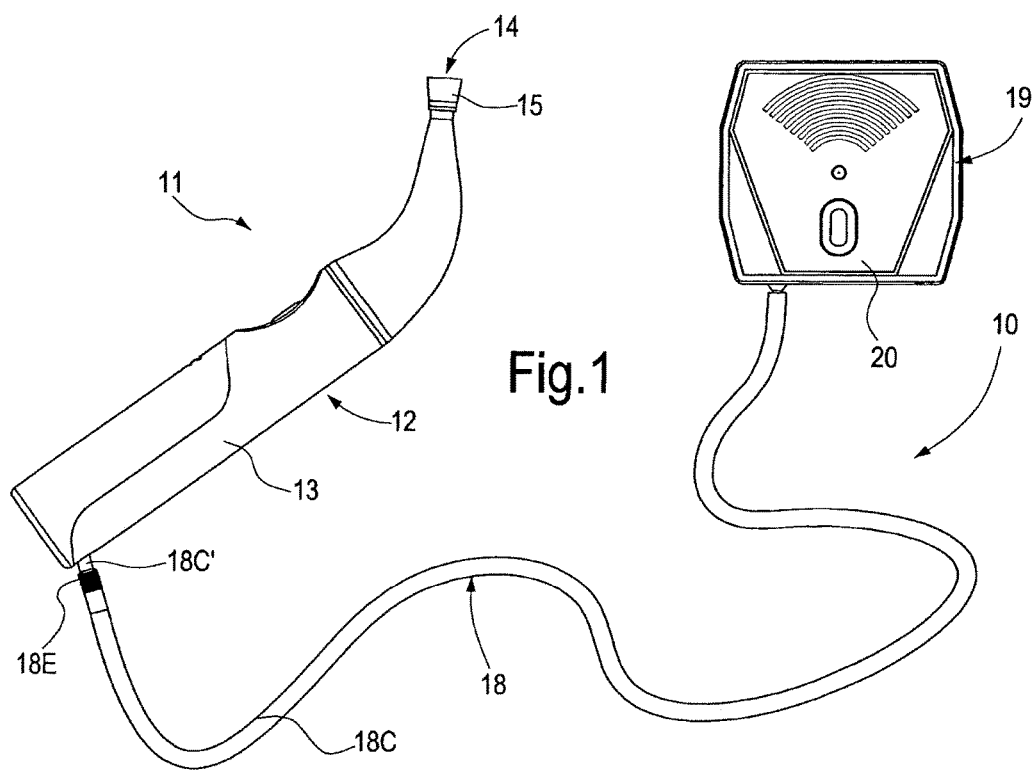
FIG. 1 is a schematic view of an embodiment of a device for whitening teeth.
Figure 2:
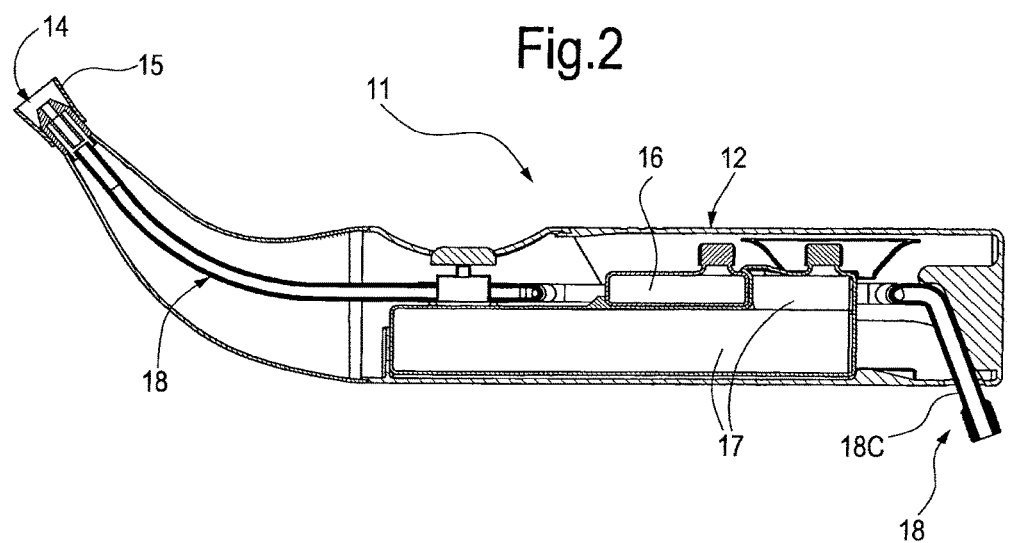
FIG. 2 is a longitudinal section of the whitening product dispenser of the device of FIG. 1.

With reference to FIGS. 1 and 2 referred to above, a first embodiment of a device for whitening teeth is labelled 10 in its entirety.

The device 10 comprises a dispenser 11 which, in this embodiment, is formed by a main body 12, in use a handpiece, which must be gripped by the user and which therefore comprises a zone to be gripped 13. It shall be understood that said zone to be gripped may be the entire outer extension of said body, depending on user preferences.

Said dispenser comprises an ejecting nozzle 14, preferably provided at one end of the main body 12, from which the flow of whitening product comes out, as described in more detail below. For example, associated with the ejecting nozzle 14 there is a cap 15 for localising the ejecting zone or product concentrator, which allows the flow of product to be kept in a limited zone, precisely controlling the zone of the teeth on which the product is to be distributed.

There is a first tank 16 of part of the whitening product, such as whitening powder (where the term powder refers to particulate of material in the solid state with very small particle size measurement), preferably containing sodium acid carbonate. More preferably, said powder also comprises pink Himalayan salt. Even more preferably, said powder also comprises sage and/or lemon and/or peppermint essential oil.

Preferably, in this example, said powder comprises
sodium acid carbonate, preferably between 70% and 90% of the weight of the compound,
pink Himalayan salt, preferably between 5% and 30% of the weight of the compound, in the case of a liquid mixture, water or physiological salt solution, preferably between 5% and 20% of the weight of the compound, one or more of the following essential oils preferably being present: lemon essential oil between 0.2 and 2% of the weight of the compound, sage essential oil between 0.2 and 1% of the weight of the compound, peppermint essential oil between 0.2 and 2% of the weight of the compound.

In other embodiments the product may contain abrasive diamond powder.

Other types of whitening products are possible.

In this example, there is also a second tank 17 of product in liquid form, preferably water or physiological salt solution. Before coming out of the ejecting nozzle 14, the liquid and the powder are mixed, by suitable means, described in more detail below, designed to mix the two components, liquid and solid, to produce the whitening product which makes contact with the teeth.

In this example, both the first tank 16 with the whitening powder, and the second tank 17 with the liquid, are fixed to the dispenser in such a way that they move together with the dispenser 11 during the movements of the hand of the user. In particular, they are contained inside the main body 12.

The device comprises a duct 18 leading to the ejecting nozzle 14 and operatively connected to a pressure energy source 19, 119, which, in this example, is a compressor 20, which produces a flow of pressurised air towards the nozzle 14.

The duct 18 comprises, along an intermediate position of it, an initial part 18C which forks into two stretches 18A and 18B which are then joined to one another again in the final stretch 18D leading to the nozzle 14. A first stretch 18A is operatively connected to the first tank 16, for example by two small tubes 18A' extending laterally from the first stretch 18A and leading into the tank. The passage of the flow of air at high speed through said first stretch of duct causes the suction and intake into the stretch 18A and therefore into the duct 18, of the whitening powder contained in the tank, by "Venturi effect".

Similarly, a second stretch 18B is operatively connected to the second tank 17, for example by two small tubes 18B' extending laterally from the second stretch 18B and leading into the second tank. The passage of the flow of air through said second stretch of duct causes the suction and intake into the second stretch 18B and therefore into the duct 18, of the liquid contained in the tank, by "Venturi effect".

The two stretches 18A and 18B together with the final stretch 18D in which these two first and second stretches are joined to one another, form the mixing means for mixing the water and the whitening powder. In fact, when the water and the powder reach the final stretch 18D, the powder and the water make contact with each other, mixing together until they come out of the nozzle 14. During use, the teeth are struck by a fast jet of liquid and powder coming out of the nozzle 14. The jet of liquid and powder has the dual effect of supplying a hygiene effect on the teeth and at the same time a whitening effect.

The initial stretch 18C of the duct 18 is, for example, made of a flexible hose connected to the delivery outlet of the compressor. Said initial stretch 18C comprises a reversible joint zone 18E for joining to the inlet of the main body 12, with a sub-stretch 18C' inside the main body, in such a way that the latter can be separated from the compressor 20.

The dispenser 11 comprises an operating push-button 21, preferably positioned on the main body 12. For example, said push-button controls a valve which intercepts the flow along the final stretch 18D of the duct 18. In other embodiments, said push-button could also be positioned at other points of the duct 18, for example along the initial stretch 18C. Moreover, the operating push-button may not be associated with any valve (or even be associated with the valve and with other controls) but simply control compressor switch on or switch off (and/or operate other functions on the compressor or on other parts of the device). In the latter case, electrical connections are necessary, for example one or more cables operatively connected to the compressor, which can also be integrated in the flexible hose 18C. Obviously, in the case of functions linked to the compressor or other functions, said push-button could also be positioned on the outer casing in which the compressor 20 is integrated.

The two tanks 16 and 17 are refillable, for example by means of removable caps which allow access to the tank. In this embodiment the main body 12, formed by a multi-part shell structure, can be opened to access the tanks 16 and 17.

In other embodiments (not illustrated in the accompanying drawings) one or both of said tanks may be non-refillable tanks and therefore substitutable once empty, in use "disposable" cartridges.

The compressor may be powered by electricity from the mains, by means of a suitable connection, or by a rechargeable battery associated with the compressor. For example, the compressor may have a pressure capacity of between approximately 1.4 bar and 2.2 bar, preferably an operating capacity of around 1.8 bar.

In other embodiments, as is schematically illustrated in FIG. 4, the compressor (now labelled 120) may be integrated in the dispenser 11, for example inserted in the main body 12, or it may be fixed to the main body in such a way that when the hand of the user gripping the main body moves, the compressor performs the same movement, as if the dispenser and the compressor were one unit.

FIG. 5 (the number references corresponding to parts of the device which are unchanged compared with the preceding figures keep the same numbering as in said figures) shows a whitening product dispensing device, comprising a pressure energy source 219 of the type which can be used until finished, for example consisting of a pressurised air can 220, of the commercial type, connected to the duct 18 with a valve 220A and a valve operating control, for example a push-button 220B, interposed between them. The can 220 may be substituted once finished (empty).

FIG. 6 shows a whitening product dispensing device 311 in the form of a spray can containing the whitening product (for example, the powder described above with physiological salt solution or water or another liquid, or only powder, or other mixtures or compounds) and a pressurised gas, for example of the type commonly used in spray cans, with the ejecting nozzle 314 provided, or integrated, on the valve of said spray can, which may comprise a directing tube 314A. In use, the body of the spray can is the main body 312 and also forms the whitening product tank 316, as well as the pressure energy source 319.

Preferably, in this example, the whitening product contained in the spray can is a mixture of
  sodium acid carbonate, preferably between 70% and 90% of the weight of the compound,
  pink Himalayan salt, preferably between 5% and 30% of the weight of the compound;
  one or more of the following essential oils may preferably be present: lemon essential oil between 0.2 and 2% of the weight of the compound, sage essential oil between 0.2 and 1% of the weight of the compound, peppermint essential oil between 0.2 and 2% of the weight of the compound.

There may be abrasive diamond powder present.

Other types of compositions for the whitening product contained in the can are possible. For example, one or more of the components just referred to may not be present.

The invention also relates to use of a spray can for whitening teeth, by application of the whitening product using a nozzle directly on the teeth, the can containing a whitening product mixture, for example having a composition as referred to above or with just one or several of the components indicated.

It shall be understood that what is illustrated only represents possible non-limiting embodiments of the invention, whose forms and positions may vary without thereby departing from the scope of the basic inventive concept of the invention. The presence of any number references in the appended claims is intended only to facilitate their reading in light of the preceding description and the accompanying drawings and does not in any way limit the scope of protection.

The invention claimed is:

1. A device for whitening teeth, comprising a dispenser (11) equipped with a zone to be gripped (13) by the user and a nozzle (14) for ejecting a flow of whitening product, characterised in that the device comprises a first tank (16) comprising at least part of the whitening product in a powder form or a liquid mixture, fixed to said dispenser (11) in such a way as to move together with said dispenser during movements of a hand of the user, and a pressure energy source (19, 119) comprising a compressor; said device comprising a second tank (17) comprising a product in liquid form; said device comprising a means for mixing said at least part of the whitening product and said product in liquid form, the mixing means comprising a duct (18) leading to said nozzle (14) and operatively connected to said pressurised energy source (19, 119) from which, on command, a flow of gas extends; said duct (18) comprising a first stretch (18A) and a second stretch (18B); said first tank (16) being connected to an intermediate portion of the first stretch (18A) so that the passage of the flow of gas through said intermediate portion of said first stretch (18A) causes the suction and intake into the duct of said at least part of the whitening product by Venturi effect; said second tank (17) being connected to an intermediate portion of the second stretch (18B) so that the passage of the flow of gas through said intermediate portion of said second stretch (18B) causes the suction and intake into the duct (18) of said product in liquid form by Venturi effect; said at least part of the whitening product and said product in liquid form mixing before corning out of the nozzle (14).

2. The device according to claim 1, wherein said powder or liquid mixture comprises
  (a) sodium acid carbonate, and
  (b) pink Himalayan salt.

3. The device according to claim 2, wherein said at least part of the whitening product comprises abrasive diamond powder.

4. The device according to claim 2, wherein when said at least part of the whitening product is in the form of the liquid mixture, the liquid mixture comprises water or a physiological salt solution.

* * * * *